US005449776A

United States Patent [19]

Vignali et al.

[11] Patent Number: 5,449,776

[45] Date of Patent: Sep. 12, 1995

[54] PIPERIDINE-TRIAZINE COMPOUNDS FOR USE AS LIGHT STABILIZERS, HEAT STABILIZERS AND OXIDATION STABILIZERS FOR ORGANIC MATERIALS

[75] Inventors: Graziano Vignali; Fabrizio Guizzardi; Graziano Zagnoni, all of Bologna, Italy

[73] Assignee: Ciba-Geigy Corporation, Ardsley, N.Y.

[21] Appl. No.: 249,004

[22] Filed: May 25, 1994

[30] Foreign Application Priority Data

Jun. 3, 1993 [IT] Italy .............................. MI93A1164

[51] Int. Cl.$^6$ .................... C07D 403/12; C07D 403/14

[52] U.S. Cl. .................................... 544/198; 540/543; 540/598; 544/113; 544/194; 544/207; 544/209; 544/212

[58] Field of Search ............... 544/113, 198, 207, 209, 544/212, 194; 540/543, 598

[56] References Cited

U.S. PATENT DOCUMENTS

| | | | |
|---|---|---|---|
| 4,102,858 | 7/1978 | Minagawa et al. | 546/188 |
| 4,578,472 | 3/1986 | Yoshimura et al. | 546/188 |
| 4,670,480 | 6/1987 | Morrone | 523/115 |
| 4,670,488 | 6/1987 | Maegawa et al. | 546/188 |
| 4,670,489 | 6/1987 | Yakahashi et al. | 524/103 |
| 4,883,831 | 11/1989 | Nelson et al. | 544/198 |
| 4,883,860 | 11/1989 | Nelson et al. | 544/198 |

FOREIGN PATENT DOCUMENTS

| | | |
|---|---|---|
| 0172413 | 2/1986 | European Pat. Off. . |
| 0253007 | 1/1988 | European Pat. Off. . |
| 0314472 | 5/1989 | European Pat. Off. . |
| 0354185 | 2/1990 | European Pat. Off. . |
| 0373778 | 6/1990 | European Pat. Off. . |
| 0373779 | 6/1990 | European Pat. Off. . |
| 0410934 | 1/1991 | European Pat. Off. . |
| 3533451 | 3/1987 | Germany . |
| 2176473 | 12/1986 | United Kingdom . |

OTHER PUBLICATIONS

C.A. 107:41080x (1987).

Derwent 92-395362/48, 1992.

*Primary Examiner*—Yogendra N. Gupta

*Attorney, Agent, or Firm*—Luther A. R. Hall

[57] ABSTRACT

Novel piperidine compounds of the formula (I) are suitable for use as light stabilizers, heat stabilizers and oxidation stabilizers for organic materials.

The definitions of $R_1$, $R_2$, $R_3$, $R_4$, $R_5$, A and n in the formula (I) are given in the text.

(I)

$$\left[ R_1-N\langle\text{2,2,6,6-tetramethylpiperidin-4-yl}\rangle-A-\overset{O}{\overset{\|}{C}}-R_2-\underset{R_3}{\underset{|}{N}}-\text{(1,3,5-triazine-2,4-diyl, 6-}R_4\text{)}- \right]_n R_5$$

6 Claims, No Drawings

PIPERIDINE-TRIAZINE COMPOUNDS FOR USE AS LIGHT STABILIZERS, HEAT STABILIZERS AND OXIDATION STABILIZERS FOR ORGANIC MATERIALS

The present invention relates to novel piperidine compounds, to their use as light stabilizers, heat stabilizers and oxidation stabilizers for organic materials, in particular synthetic polymers, and to the organic materials thus stabilized.

The stabilization of synthetic polymers by piperidine derivatives of amino acids has been reported in various patents, in particular U.S. Pat. Nos. 4,102,858, 4,578,472, 4,670,488, 4,670,489, 4,883,831 and 4,883,860, in EP Patents 172.413 and 253.007, in DE Patent 3.533.451, in GB-A 2 176 473 and in Japanese Application No. Hei 4 295 465.

The present invention relates to novel compounds of the formula (I)

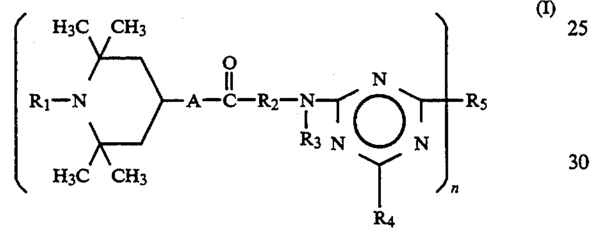

in which $R_1$ is hydrogen, $C_1$-$C_8$alkyl, O, OH, $CH_2CN$, $C_1$-$C_{18}$alkoxy, $C_5$-$C_{12}$cycloalkoxy, $C_3$-$C_6$alkenyl, $C_7$-$C_9$phenylalkyl unsubstituted or mono-, di- or tri-substituted on the phenyl by $C_1$-$C_4$alkyl, or aliphatic $C_1$-$C_8$acyl, A is —O— or $R_6$—N— with $R_6$ being hydrogen or $C_1$-$C_{12}$alkyl, $R_2$ is $C_1$-$C_{10}$alkylene, $R_3$ is hydrogen, $C_1$-$C_{18}$alkyl, $C_5$-$C_{12}$cycloalkyl unsubstituted or mono-, di- or tri-substituted by $C_1$-$C_4$alkyl, $C_7$-$C_9$phenylalkyl unsubstituted or mono-, di- or tri-substituted on the phenyl by $C_1$-$C_4$alkyl, tetrahydrofurfuryl or a group of the formula (II)

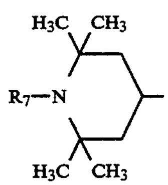

where $R_7$ is as defined for $R_1$ or $C_2$-$C_4$alkyl substituted in the 2, 3- or 4-position by $C_1$-$C_8$alkoxy, by di($C_1$-$C_4$alkyl)amino or by a group of the formula (III)

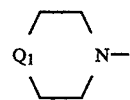

where $Q_1$ is a direct bond, —O—, —$CH_2$—, —$CH_2CH_2$— or

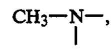

or $R_3$ is also a group of the formula (IV)

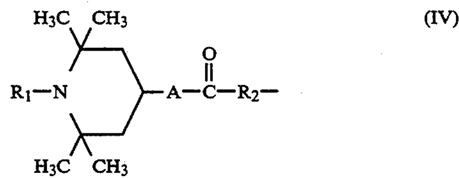

$R_4$ is a group of the formula (V)

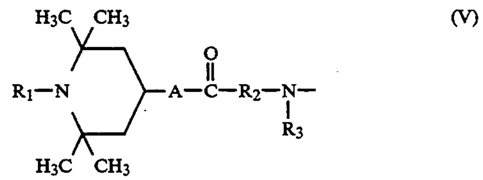

or a group of the formula (III) or one of the groups of the formulae (VIa)-(VIe)

$R_8$—N($R_9$)— (VIa)

$R_{10}$—O— (VIb)

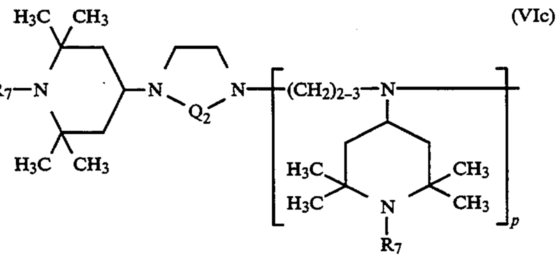

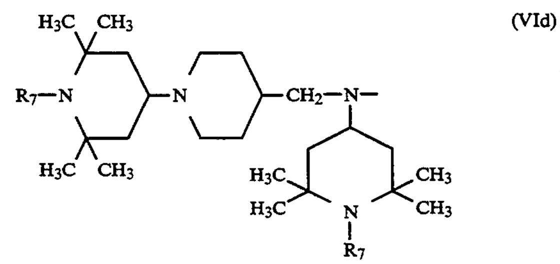

-continued

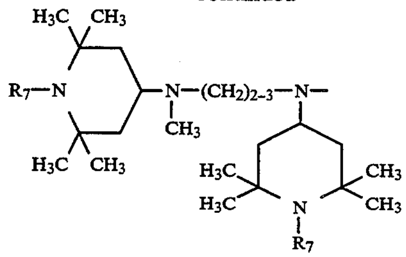

(VIe)

in which $R_7$ is as defined above, $R_8$, $R_9$ and $R_{10}$ which can be identical or different are as defined for $R_3$, or $R_{10}$ is also $C_3$–$C_{18}$alkenyl or phenyl unsubstituted or mono-, di- or tri-substituted by $C_1$–$C_4$alkyl or $C_1$–$C_4$alkoxy, $Q_2$ is —CO—, —$CH_2CH_2$—, —COCO—, —$CH_2CO$— or —$COCH_2CO$— and p is zero or 1, n is 2, 3 or 4 and, if n is 2, $R_5$ is one of the groups of the formulae (VIIa)-(VIIc)

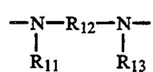

(VIIa)

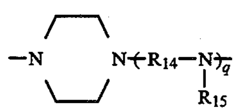

(VIIb)

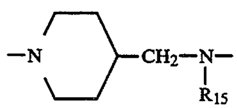

(VIIc)

in which $R_{11}$, $R_{13}$ and $R_{15}$ which can be identical or different are as defined for $R_3$, or $R_{11}$ and $R_{13}$ are also a group of the formula (IV), $R_{12}$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_{12}$alkylene interrupted by a 1,4-piperazinediyl group or by 1, 2 or 3 oxygen atoms or by 1 or 2

$R_{16}$N— groups, where $R_{16}$ is as defined for $R_3$ or is aliphatic $C_1$–$C_{12}$acyl or ($C_1$–$C_{12}$alkoxy)carbonyl, or $R_2$ is also a group

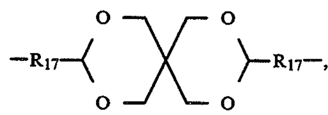

$R_{14}$ and $R_{17}$ are $C_2C_6$alkylene and q is zero or 1, and if n is 3, $R_5$ is a group of the formula (VIIIa) or (VIIIb)

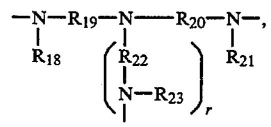

(VIIIa)

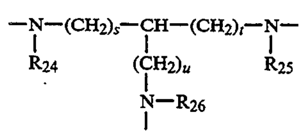

(VIIIb)

in which $R_{18}$, $R_{21}$, $R_{23}$, $R_{24}$, $R_{25}$ and $R_{26}$ which can be identical or different are as defined above for $R_{11}$ and $R_{13}$, $R_{19}$, $R_{20}$ and $R_{22}$ which can be identical or different are $C_2$–$C_6$alkylene, r and u are zero or 1, and s and t which can be identical or different are integers from 2 to 6, and, if n is 4, $R_5$ is a group of the formula (IX)

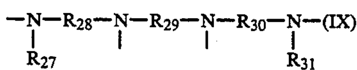

(IX)

in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_6$alkylene.

Examples of alkyl having not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Preferred examples of $C_2$–$C_4$alkyl substituted by a group of the formula (III) are the groups

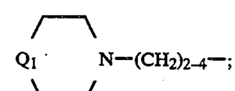

the group

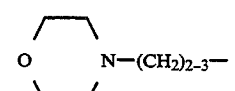

is particularly preferred.

Examples of alkoxy having not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. Preferred examples of $R_1$ and $R_7$ are $C_6$–$C_{12}$alkoxy, in particular heptoxy and octoxy.

Examples of $C_5$–$C_{12}$cycloalkyl unsubstituted or mono-, di- or tri-substituted by $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

Examples of $C_5$–$C_{12}$cycloalkoxy $R_1$ and $R_7$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are allyl, 2-methylallyl, butenyl, hexenyl, undecenyl and octadecenyl. Alkenyls in which the carbon atom in the 1-position is saturated are preferred; allyl is particularly preferred.

Representative examples of phenyl mono-, di- or tri-substituted by $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_9$phenylalkyl unsubstituted or mono-, di- or tri-substituted on the phenyl by $C_1$–$C_4$alkyl are benzyl, methylbenzyl, dimethylbenzyl, trimethylbenzyl, 2-butylbenzyl and 2-phenylethyl. Benzyl is preferred.

Representative examples of aliphatic acyl having not more than 12 carbon atoms are acetyl, propionyl, butyryl, isobutyryl, pentanoyl, hexanoyl, heptanoyl, octanoyl, 2-ethylhexanoyl, decanoyl, undecanoyl, dodecanoyl, acryloyl, crotonyl and 10-undecenoyl. $C_1$–$C_8$Alkanoyl and $C_3$–$C_8$alkenoyl are particularly preferred.

Examples of alkylene having not more than 12 carbon atoms are ethylene, propylene, trimethylene, 2-methyltrimethylene, 2,2-dimethyltrimethylene, tetramethylene, pentamethylene, hexamethylene, trimethylhexamethylene, octamethylene, decamethylene and dodecamethylene.

A preferred example of $C_4$–$C_{12}$alkylene $R_{12}$ interrupted by a 1,4-piperazinediyl group is the group

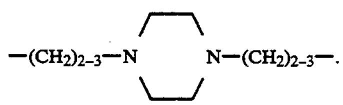

Examples of $C_4$–$C_{12}$alkylene interrupted by 1, 2 or 3 oxygen atoms are 4-oxaheptane-1,7-diyl, 4,7-dioxadecane-1,10-diyl, 4,9-dioxadodecane-1,12-diyl and 4,7,10-trioxatridecane-1,13-diyl.

Representative examples of $C_4$–$C_{12}$alkylene $R_{12}$ interrupted by 1 or 2

$R_{16}$—N— groups are the groups

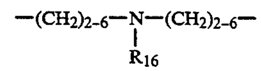

and

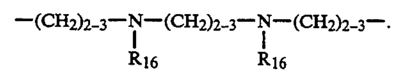

Representative examples of groups having 1 or 2 $C_5$–$C_7$cycloalkylene groups are cyclohexylene, methylcyclohexylene, cyclohexylenedimethylene, methylenedicyclohexylene and the group

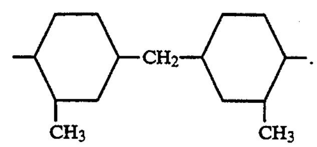

Phenylenedimethylene is the preferred example of phenylenedi($C_1$–$C_4$alkylene).

Preferred definitions of $R_1$ and $R_7$ are hydrogen, $C_1$–$C_4$alkyl, OH, $C_6$–$C_{12}$alkoxy, $C_5$–$C_8$cycloalkoxy, allyl, benzyl or acetyl, in particular hydrogen or methyl.

Those compounds of the formula (I) are preferred in which A is —O— or $R_6$—N— with $R_6$ being hydrogen or $C_1$–$C_{10}$alkyl, $R_2$ is $C_1$–$C_{10}$alkylene, $R_3$ is hydrogen, $C_1$–$C_{14}$ alkyl, $C_5$–$C_8$cycloalkyl unsubstituted or mono-, di- or tri-substituted by $C_1$–$C_4$alkyl, benzyl unsubstituted or mono-, di- or tri-substituted on the phenyl by $C_1$–$C_4$alkyl, tetrahydrofurfuryl, a group of the formula (II), $C_2$–$C_3$alkyl substituted in the 2- or 3-position by $C_1$–$C_4$alkoxy, by di($C_1$–$C_4$alkyl)amino or by a group of the formula (III), where $Q_1$ is a direct bond, —O—, —$CH_2$— or —$CH_2CH_2$—, or $R_3$ is also a group of the formula (IV), $R_4$ is a group of the formula (V) or a group of the formula (III) or one of the groups of the formulae (VIa)–(VIe), in which $R_8$, $R_9$ and $R_{10}$ which can be identical or different are as defined for $R_3$, or $R_{10}$ is also $C_3$–$C_{12}$alkenyl or phenyl unsubstituted or mono-, di- or tri-substituted by $C_1$–$C_4$alkyl or $C_1$–$C_4$alkoxy, $Q_2$ is —CO—, —$CH_2CH_2$—, —COCO— or —$COCH_2CO$—, p is zero or 1 and n is 2, 3 or 4, and, if n is 2, $R_5$ is one of the groups of the formulae (VIIa)–(VIIc) in which $R_{11}$, $R_{13}$ and $R_{15}$ which can be identical or different are as defined above for $R_3$ or $R_{11}$ and $R_{13}$ are also a group of the formula (IV), $R_{12}$ is $C_2$–$C_{10}$alkylene, cyclohexylene, cyclohexylenedimethylene, methylenedicyclohexylene, phenylenedimethylene, $C_4$–$C_{10}$alkylene interrupted by a 1,4-piperazinediyl group or by 1, 2 or 3 oxygen atoms or by 1 or 2

$R_{16}$—N— groups, where $R_{16}$ is as defined above for $R_3$ or is aliphatic $C_1$–$C_8$acyl or ($C_1$–$C_8$alkoxy)carbonyl, or $R_2$ is also a group

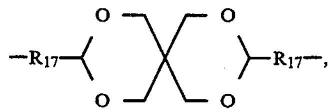

$R_{14}$ and $R_{17}$ are $C_2$–$C_4$alkylene and q is zero or 1, and, if n is 3, $R_5$ is a group of the formula (VIIIa) or (VIIIb), in which $R_{18}$, $R_{12}$, $R_{23}$, $R_{24}$, $R_{25}$ and $R_{26}$ which can be identical or different are as defined above for $R_{11}$ and $R_{13}$, $R_{19}$, $R_{20}$ and $R_{22}$ which can be identical or different are $C_2$–$C_4$alkylene, r and u are zero or 1 and s and t which can be identical or different are integers from 3 to 6 and, if n is 4, $R_5$ is a group of the formula (IX) in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_4$alkylene.

Those compounds of the formula (I) are particularly preferred in which A is —O— or $R_6$—N—
  | with $R_6$ being hydrogen or $C_1$–$C_8$alkyl, $R_2$ is $C_1$–$C_8$alkylene, $R_3$ is hydrogen, $C_1$–$C_{12}$alkyl, cyclohexyl unsubstituted or mono-, di- or tri-substituted by $C_1$–$C_4$alkyl, benzyl, tetrahydrofurfuryl, a group of the formula (II), $C_2$–$C_3$alkyl substituted in the 2- or 3-position by methoxy, by ethoxy, by dimethylamino, by diethylamino or by a 4-morpholinyl group, or $R_3$ is also a group of the formula (IV), $R_4$ is a group of the formula (V) or a 4-morpholinyl group or one of the groups of the formulae (VIa)-(VIe) in which $R_8$, $R_9$ and $R_{10}$ which can be identical or different are as defined above for $R_3$, or $R_{10}$ is also $C_3$–$C_{11}$alkenyl or phenyl, $Q_2$ is —CO—, —$CH_2CH_2$— or —COCO—, p is zero or 1 and n is 2, 3 or 4, and, if n is 2, $R_5$ is one of the groups of the formulae (VIIa)-(VIIc) in which $R_{11}$, $R_{13}$ and $R_{15}$ which can be identical or different are as defined above for $R_3$, or $R_{11}$ and $R_{13}$ are also a group of the formula (IV), $R_{12}$ is $C_2$–$C_8$alkylene, cyclohexylenedimethylene, methylenedicyclohexylene, phenylenedimethylene, $C_4$–$C_{10}$alkylene interrupted by a 1,4-piperazinediyl group or by 1, 2 or 3 oxygen atoms or by 1 or 2

$R_{16}$—N—
  | groups, where $R_{16}$ is as defined above for $R_3$ or is aliphatic $C_1$–$C_4$acyl or ($C_1$–$C_4$alkoxy)carbonyl, or $R_{12}$ is also a group

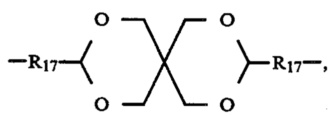

$R_{14}$ and $R_7$ are $C_2$–$C_4$alkylene and q is zero or 1, and, if n is 3, $R_5$ is a group of the formula (VIIIa) or (VIIIb) in which $R_{18}$, $R_{21}$, $R_{23}$, $R_{24}$, $R_{25}$ and $R_{26}$ which can be identical or different are as defined above for $R_{11}$ and $R_{13}$, $R_{19}$, $R_{20}$ and $R_{22}$ which can be identical or different are $C_2$–$C_4$alkylene, r and u are zero or 1 and s and t which can be identical or different are integers from 3 to 5, and, if n is 4, $R_5$ is a group of the formula (IX) in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_4$alkylene.

Those compounds of the formula (I) are of special interest in which A is —O— or $R_6$—N—
  | with $R_6$ being hydrogen or $C$–$C_4$alkyl, $R_2$ is $C_1$–$C_5$alkylene, $R_3$ is hydrogen, $C_1$–$C_8$alkyl, cyclohexyl, a group of the formula (II) or a group of the formula (IV), $R_4$ is a group of the formula (V) or a 4-morpholinyl group or one of the groups of the formulae (VIa)-(VIe) in which $R_8$, $R_9$ and $R_{10}$ which can be identical or different are as defined above for $R_3$, $Q_2$ is —CO— or —$CH_2CH_2$—, p is zero or 1 and n is 2, 3 or 4, and, if n is 2, $R_5$ is one of the groups of the formulae (VIIa)-(VIIc) in which $R_{11}$, $R_{13}$ and $R_{15}$ which can be identical or different are as defined above for $R_3$, or $R_{11}$ and $R_{13}$ are also a group of the formula (IV), $R_2$ is $C_2$–$C_6$alkylene, cyclohexylenedimethylene, methylenedicyclohexylene, $C_6$–$C_{10}$alkylene interrupted by a 1,4-piperazinediyl group or by 2 or 3 oxygen atoms or by a group

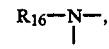

where $R_{16}$ is as defined above for $R_3$, $R_{14}$ is $C_2$–$C_3$alkylene and q is zero or 1, and, if n is 3, $R_5$ is a group of the formula VIIIa) or (VIIIb) in which r is zero, $R_{18}$, $R_{21}$, $R_{24}$, $R_{25}$ and $R_{26}$, which can be identical or different are as defined above for $R_{11}$ and $R_{13}$, $R_{19}$ and $R_{20}$ which can be identical or different are $C_2$–$C_3$alkylene, u is zero or 1 and s and t which can be identical or different are integers from 3 to 5, and, if n is 4, $R_5$ is a group of the formula (IX) in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_3$alkylene.

Those compounds of the formula (I) are of particular interest in which $R_1$ and $R_7$ are hydrogen or methyl, A is —O— or —NH—, $R_2$ is $C_1$–$C_2$alkylene, $R_3$ is hydrogen, $C_1$–$C_4$alkyl, 2,2,6,6-tetramethyl-4-piperidyl or 1,2,2,6,6-pentamethyl-4-piperidyl, $R_4$ is a group of the formula (V) or a group of the formula (VIa) or (VIb) in which $R_8$ and $R_9$ which can be identical or different are as defined above for $R_3$, $R_{10}$ is 2,2,6,6-tetramethyl-4-piperidyl or 1,2,2,6,6-pentamethyl-4-piperidyl and n is 2, 3 or 4, and, if n is 2, $R_5$ is a group

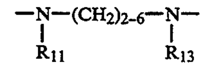

or a group

-continued

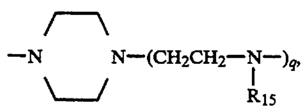

in which $R_{11}$, $R_{13}$ and $R_{15}$ which can be identical or different are as defined above for $R_3$, and q is zero or 1, and, if n is 3, $R_5$ is a group

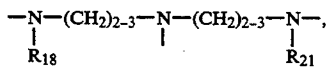

and, if n is 4, $R_5$ is a group

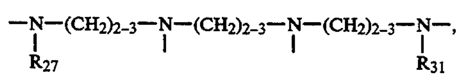

and $R_{18}$, $R_{21}$, $R_{27}$ and $R_{31}$ are as defined above for $R_3$.

The compounds of the present invention can be prepared by processes known per se.

According to process A, the compounds of the formula (I) can be prepared by reacting, in any order and in the appropriate molar ratios, cyanuric chloride with compounds of the formulae (Xa)-(Xc)

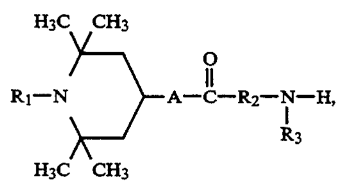

(Xa)

$R_4$—H, (Xb)

$R_5$—$(H)_n$ (Xc)

The reaction is carded out in an inert organic solvent, for example toluene, xylene, trimethylbenzene, t-amyl alcohol or a mixture of t-amyl alcohol in any proportions with said hydrocarbons, in the presence of a preferably inorganic base, for example sodium or potassium hydroxide or carbonate, at temperatures from −20° to 200° C., preferably from −10° to 180° C.

According to process B, the compounds of the formula (I) can be obtained by initially preparing the corresponding compounds in which the group

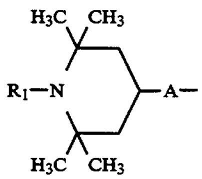

is replaced by a $C_1$-$C_4$alkoxy group and successively reacting the alkyl derivatives obtained with the appropriate molar quantity of a compound of the formula (XI)

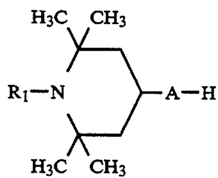

(XI)

in the presence of a catalyst such as an alkali metal, a $C_1$-$C_4$alkoxide or amide or hydride of an alkali metal, a $C_1$-$C_4$alkoxide of Ti(IV) or dibutyltin oxide, the reaction being carded out in the absence of a solvent or in an inert organic solvent, for example toluene, xylene or trimethylbenzene, at temperatures from 100° to 200° C., preferably from 110° to 180° C.

When working according to process B, it is possible in the reaction with cyanuric chloride, if A is —O—, to use a compound of the formula (XI) in which A is —O—, as temporary acceptor of the hydrochloric acid released, the hydrochloride formed being subsequently neutralized with a hydroxide or $C_1$-$C_4$alkoxide of sodium or potassium to reform the free base, which thus becomes available for the transesterification reaction.

The various stages of the reactions can be carded out in a single reactor and in the same solvent or in different solvents, without isolation of the intermediates or after separating and, if desired, purifying these.

The compounds of the formulae (Xa) and (XI) can be prepared by known processes; the other reagents are commercially available or can be prepared according to the state of the art.

As mentioned at the outset, the compounds of the present invention are highly effective in improving the light stability, heat stability and oxidation stability of organic materials, in particular synthetic polymers and copolymers, and are particularly suitable for stabilizing polypropylene fibres.

Examples of such organic materials which can be stabilized are:

1. Polymers of monoolefins and diolefins, for example polypropylene, polyisobutylene, polybuty-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(IID chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals beeing elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer, and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and mines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer;, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/VA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Object of the invention is also a composition comprising a material susceptible to the degradation induced by light, heat and oxidation and at least one compound of the formula I, and optionally other conventional additives for synthetic polymers.

Preferred are compositions, wherein the organic material is a synthetic polymer, for example a polyolefine, especially a polyethylene or polypropylene.

The compounds of the formula (I) are particularly suitable for improving the light stability, heat stability and oxidation stability of polyolefins, especially polyethylene and polypropylene.

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

In general, the compounds of the formula (I) can be added to the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (D with the organic materials.

Particular examples of additives which can be used in admixture with the compounds of the formula (I) are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures therof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl14-hydroxyanisole, 3,5-di-tert-butyl-4-hydroxyanisole, 3,5-di-tert-butyl-4-hydroxyphenylstearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4- octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis-(2,6-dimethyl-4-hydroxyphenyl)disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylene-bis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-burylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane 2,2-bis-(3,5-di-tert-butyl-4-hydroxyphenyl)propane, 2,2-bis-( 5-tert-butyl-4-hydroxy2-methylphenyl)-4-n-dodecylmercaptobutane, 1,1,5,5-tetra-(5-tert-butyl-4-hydroxy2-methylphenyl)pentane.

1.6. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5di-tert-butyl-4-hydroxybenzylmercaptoacetate.

1.7. Hydroxybenzoate malonates, for example dioctadecyl-2,2-bis-(3,5-di-tert-butyl-2-hydroxybenzyl)-malonate, di-octadecyl-2-(3-ten-butyl-4-hydroxy-5-methylbenzyl)-malonate, di-dodecylmercaptoethyl-2,2-bis-(3,5-di-tert-butyl-4-hydroxybenzyl)malonate, bis-[4-(1,1,3,3-tetramethylbutyl)phenyl]-2,2-bis(3,5-di-tert-butyl-4-hydroxybenzyl)malonate.

1.8. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.9. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl-)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.10. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.11. Acylaminophenols, for example 4-hydroxylauranilide, 4-hydroxystearanilide, octyl N-(3,5-di-tert-butyl-4-hydroxyphenyl)carbamate.

1.12. Esters of β-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl-)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.13. Esters of β-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.21octane.

1.14 Esters of β-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl-)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl-)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-timethylenediamine, N,N'-bis(3,5-di-tert-butyl-4-hydroxyphenylpropionyl)hydrazine.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotrizole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chlorobenzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)-phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-his[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; $[R-CH_2CH_2-COO(CH_2)_3]_2$, where R=3'-tert-butyl-4'-hydroxy-5'-2H-benzotriazol-2-ylphenyl.

2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl)resorcinol, benzoyl resorcinol, 2,4-di-tertbutylphenyl 3,5-di-tert-butyl-4-hyctroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-( 1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl- 1,3,8-triazasprio[4.5]decan-2,4-dion,bis( 1-octyloxy-2,2,6,6-tetramethylpiperidyl bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione.

2.7. Oxamides, for example 4,4'-dioctyloxyoxanilide, 2,2'-dioctyloxy-5,5'-di-tert-butoxanilide, 2,2'-didodeeyloxy-5,5'-di-tert-butoxanilide, 2-ethoxy-2'-ethoxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

2.8.2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

3. Metal deactivators, for example N,N'-diphenyloxamide, N-salicylal-N'-salicyloyl hydrazine, N,N'-bis(-salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetaladipoyl dihydrazide, N,N'-bis(salicyloyl)oxalyl dihydrazide, N,N'-bis(salicyloyl)-thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioetadecyl phosphite, distearyl pentaerythritol diphosphite, tris(2,4-di-tert-butylphenyl)-phosphite, diisodecyl pentaerythritol diphosphite, bis(2,4-di-tert-butylphenyl)pentaerythritol diphosphite, bis(2,6-di-tert-butyl-4-methylphenyl)-pentaerythfitol diphosphite, diisodecyloxypentaerythritol diphosphite, bis(2,4-di-tert-butyl-6-methylphenyl)pentaerythfitol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

4a. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis(1-hydroxy-2,2,6,6-tetramethyl-4-piperidyl)sebacate.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

11. Benzofuranones and indolinones, for example those disclosed in U.S. Pat. No. 4,325,863 or U.S. Pat. No. 4,338,244 or U.S. Pat. N. 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)-phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl-5,7-di-tert-butyl-benzofuran-2-one, 3-(3,5-dimethyl-4-pivaloyloxyphenyl)-5,7-di-tert-butyl-benzofuran-2-one.

The compounds of the present invention can also be used as stabilizers, especially as light stabilizers, for the major pan of the materials known in the an of photographic reproduction and other reproduction techniques, for example as described in Research Disclosure 1990, 31429 (pages 474–480).

Several examples of the preparation and use of the compounds of the formula (I) are reported for more detailed illustration of the present invention; these examples are given solely for illustrative purposes and do not imply any restriction.

EXAMPLE 1

Preparation of the compound of the formula

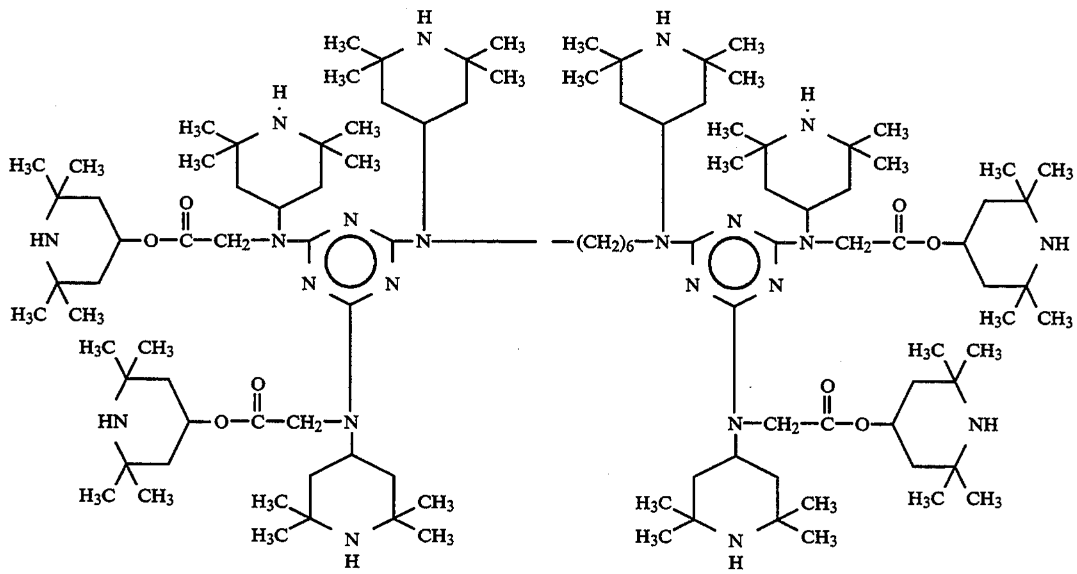

106.1 g (0.3 mol) of N-(2,2,6,6-tetramethyl-4-piperidyl)glycine 2,2,6,6-tetramethyl-4-piperidyl ester are added slowly to a solution of 27.7 g (0.15 mol) of cyanuric chloride in 280 ml of mesitylene, maintaining the temperature at 0° C.

After the end of the addition, the mixture is stirred for 2 hours at ambient temperature and 45.6 g (0.33 mol) of ground $K_2CO_3$ are added, followed by heating for 4 hours at 80° C.

After cooling to ambient temperature, 29.6 g (0.075 mol) of N,N'-bis(2,2,6,6-tetramethyl-4-piperidyl)-1,6-hexanediamine are added and this mixture is heated for 2 hours under reflux; 34.6 g (0.25 mol) of ground $K_2CO_3$ are added, followed by further heating under reflux for 10 hours, the water of reaction being azeotropically separated off. The mixture is cooled to 60° C., filtered and evaporated in vacuo. The residue is crystallized from hexane.

The product obtained melts at 187°–189° C.

Analysis for $C_{110}H_{200}N_{22}O_8$ Calculated: C=67.45%, H=10.29%, N=15.73% Found: C=66.95%, H=10.21%, N=15.57%

EXAMPLE 2

The compound of the formula

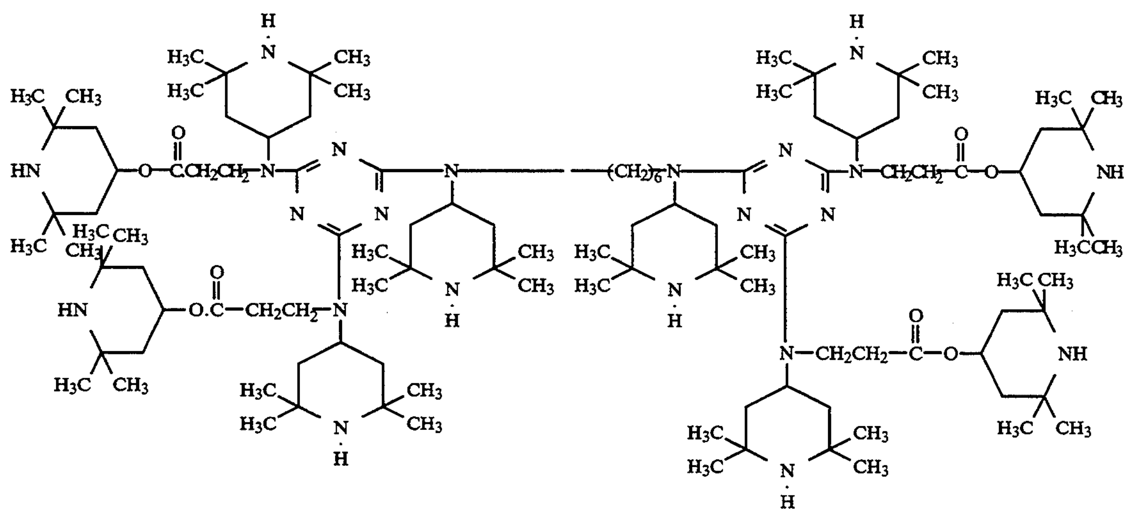

is prepared as described in Example 1, by reacting 27.7 g (0.15 mol) of cyanuric chloride with 110.3 (0.3 mol) of N-(2,2,6,6-tetramethyl-4-piperidyl)-β-alanine 2,2,6,6-tetramethyl-4-piperidyl ester and 29.6 g (0.075 mol) of N,N'-bis(2,2,6,6-tetramethyl-4-piperidyl)-1,6-hexanediamine. The product obtained melts at 136°-138° C. after purification by column chromatography.

Analysis for $C_{114}H_{208}N_{22}O_8$ Calculated: C=67.95%, H=10.40%, N=15.29% Found: C=67.25%, H=10.30%, N=15.26%

EXAMPLE 3

The compound of the formula is prepared as described in Example 1, by reacting 27.7 g (0.15 mol) of cyanuric chloride with 106.1 g (0.3 mol) of N-(2,2,6,6-tetramethyl-4-piperidyl)glycine 2,2,6,6-tetramethyl-4-piperidyl ester and 9.7 g (0,075 mol) of 1-piperazinethaneamine.

The product obtained melts at 125°-127° C. after crystallization from hexane.

Analysis for $C_{92}H_{165}N_{21}O_8$ Calculated: C=65.25%, H=9.82%, N=17.37% Found: C=64.59%, H=9.75%, N=17.26%

EXAMPLE 4

The compound of the formula

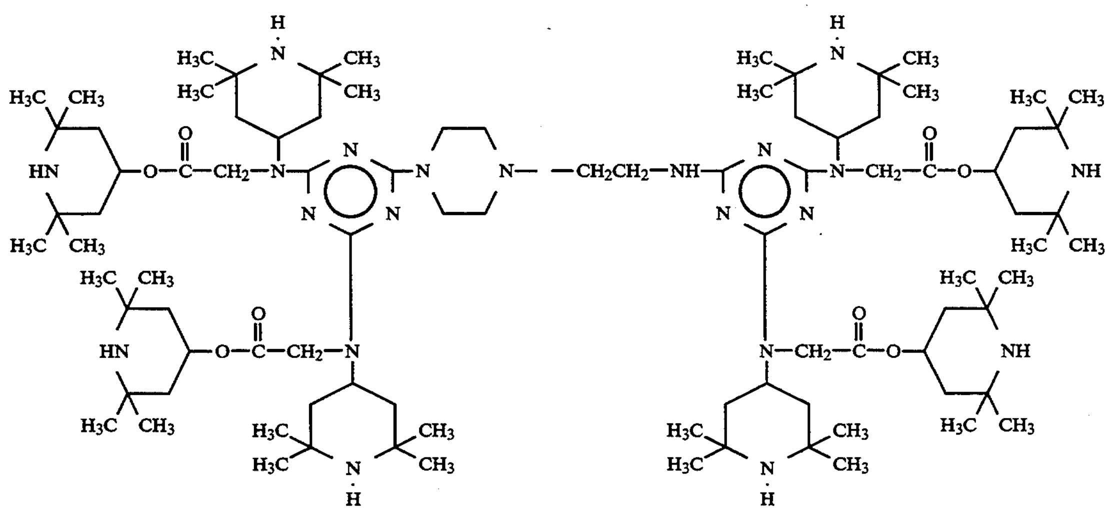

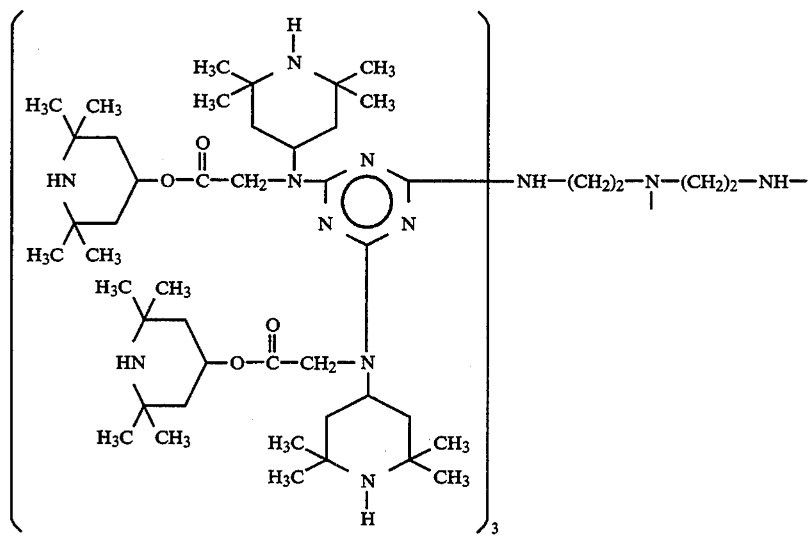

is prepared as described in Example 1 by reacting 27.7 g (0.15 mol) of cyanuric chloride with 106.1 g (0.3 mol) of N-(2,2,6,6-tetramethyl-4-piperidyl)glycine 2,2,6,6-tetramethyl-4-piperidyl ester and 5.2 g (0.05 mol) of diethylenetriamine.

The product obtained melts at 137°-139° C. after crystallization from hexane.

Analysis for $C_{133}H_{238}N_{30}O_{12}$ Calculated: C=65.21%, H=9.79%, N=17.15% Found: C=65.21%, H=9.77%, N=17.04%

EXAMPLE 5

The compound of the formula is prepared as described in Example 1 by reacting 27.7 g (0.15 mol) of cyanuric chloride with 106.1 g (0.3 mol) of N-(2,2,6,6-tetramethyl-4-piperidyl)glycine 2,2,6,6-tetramethyl-4-piperidyl ester and 19.1 g (0.05 mol) of N,N''-bis(2,2,6,6-tetramethyl-4-piperidyl)diethylenetriamine.

The product obtained melts at171°-174° C.

Analysis for $C_{157}H_{272}N_{32}O_{12}$ Calculated: C=66.48%, H=10.05%, N=16.43% Found: C=66.18%, H=10.00%, N=16.33%

EXAMPLE 6

The compound of the formula

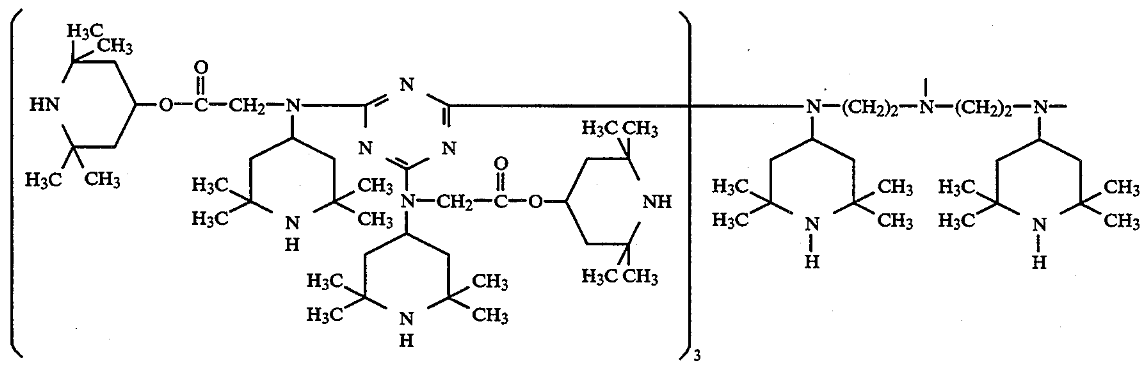

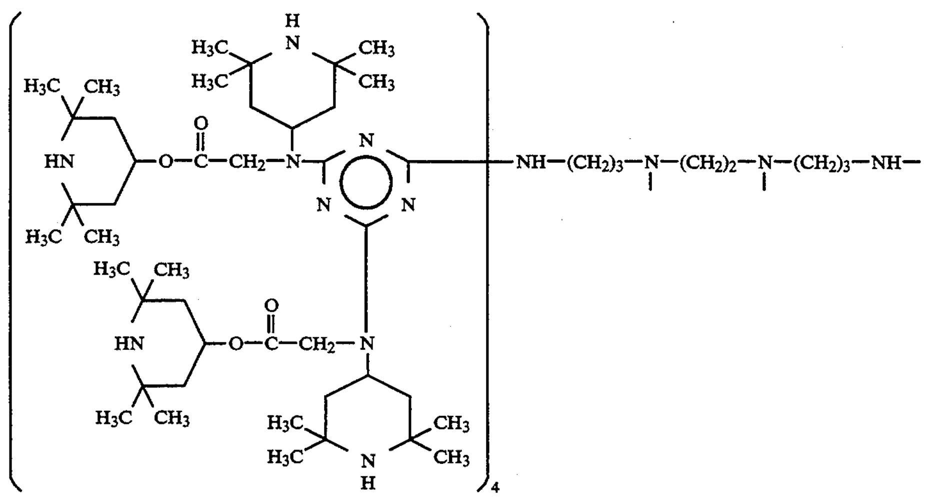

is prepared as described in Example 1, by reacting27.7 g (0.15 mol) of cyanuric chloride with 106.1 g (0.3 mol) of N-(2,2,6,6-tetramethyl-4-piperidyl)glycine 2,2,6,6-tetramethyl-4-piperidyl ester and 6.5 g (0.0375 mol) of N,N'-bis(3-aminopropyl)-1,2-ethanediamine.

The product obtained melts at 151°-153° C. after crystallization from hexane.

Analysis for $C_{180}H_{322}N_{40}O_{16}$ Calculated: C=65.46%, H=9.83%, N=16.96% Found: C=65.27%, H=9.76%, N=16.86%

EXAMPLE 7

Preparation of the compound of the formula

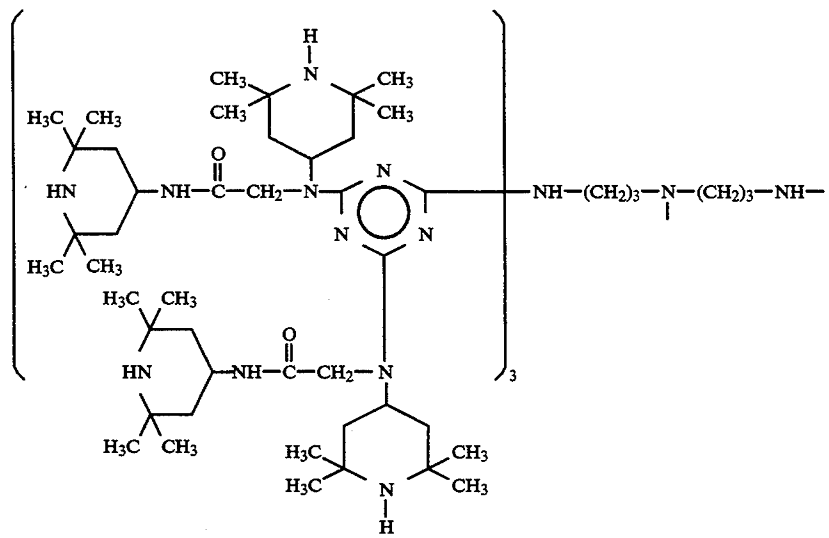

105.8 g (0.3 mol) of N-(2,2,6,6-tetramethyl-4-piperidyl)-2-[(2,2,6,6-tetramethyl-4-piperidyl)amino]-acetamide are added slowly to a solution of 27.7 g (0.15 mol) of cyanuric chloride in 280 ml of mesitylene, maintaining the temperature at between 0° and 5° C. After the end of the addition, the mixture is heated for 3 hours at 70° C. and then cooled to ambient temperature; a solution of 12 g (0.3 mol) of NaOH and 20 ml of water is added, and the mixture is stirred for 30 minutes and heated for a further 2 hours at 70° C. It is cooled to ambient temperature and stirred for 15 minutes after addition of 50 ml of water, and the aqueous phase is separated off.

6.6 g (0.05 mol) of bis(3-aminopropyl)amine are added to the organic phase thus obtained and the mixture is heated for 2 hours under reflux. It is then cooled to 50° C., 12 g (0.3 mol) of ground NaOH are added, followed by further heating under reflux for 12 hours, the water of reaction being separated off azeotropically.

After cooling to 50° C., the reaction mixture is washed with water, dried over anhydrous $Na_2SO_4$ and evaporated in vacuo.

The product obtained melts at 169°-172° C.

Analysis for $C_{135}H_{248}N_{36}O_6$ Calculated: C=65.70%, H=10.11%, N=20.40% Found: C=65.19%, H=10.01%, N=20.14%

EXAMPLE 8

Preparation of of the compound of the formula

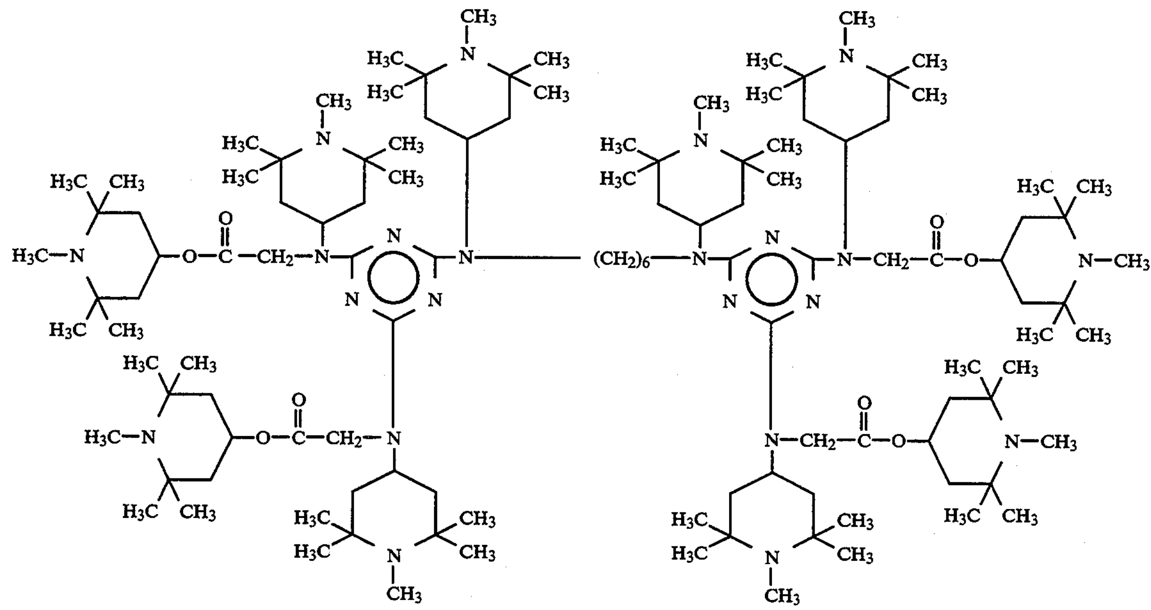

A mixture of 25 g (0.0128 mol) of the compound from Example 1 and 4.5 g (0.15 mol) of paraformaldehyde in 200 ml of t-amyl alcohol is heated for 1 hour at 80° C. In the course of 1 hour at the same temperature, 6.9 g (0.15 tool) of formic acid are then added. After the end of the addition, the mixture is heated at 80° C. for a further 2 hours.

After cooling to ambient temperature, a solution of 20.7 g (0.15 mol) of $K_2CO_3$ in 50 ml of water is added, the mixture is stirred for 30 minutes and the aqueous phase is separated off. The organic phase is dried over anhydrous $Na_2SO_4$ and evaporated in vacuo. The product obtained melts at 167°–169° C.

Analysis for $C_{120}H_{220}N_{22}O_8$ Calculated: C=68.66%, H=10.56%, N=14.68% Found: C=68.56%, H=10.46%, N=14.59%

EXAMPLE 9

The compound of the formula

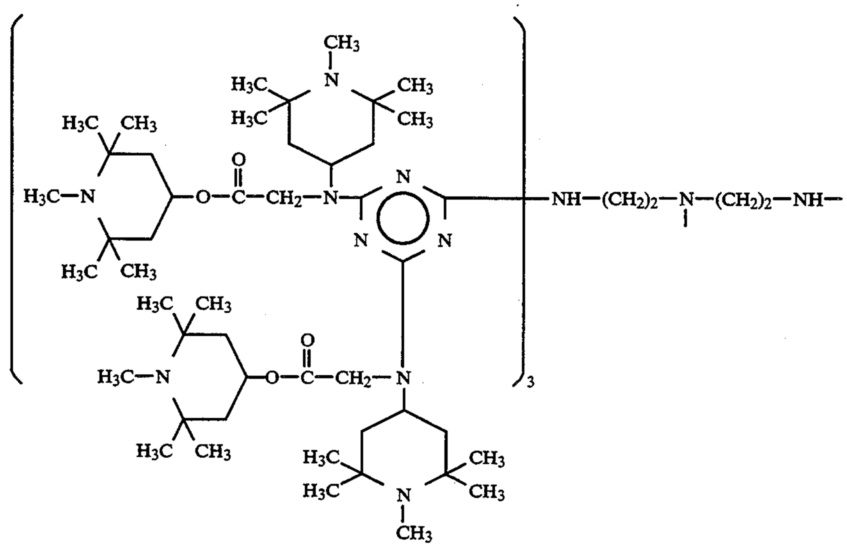

is prepared as described in Example 8, by reacting 36.7 g (0.015 mol) of the compound from Example 4 with 6 g (0.2 mol) of paraformaldehyde and 8.5 g (0.185 mol) of formic acid in 200 ml of t-amyl alcohol.

The product obtained melts at 150°–152° C.

Analysis for $C_{145}H_{262}N_{30}O_{12}$ Calculated: C=66.53%, H=10.09%, N=16.05% Found: C=66.11% H=10.07%, N=15.99%

EXAMPLE 10

The compound of the formula

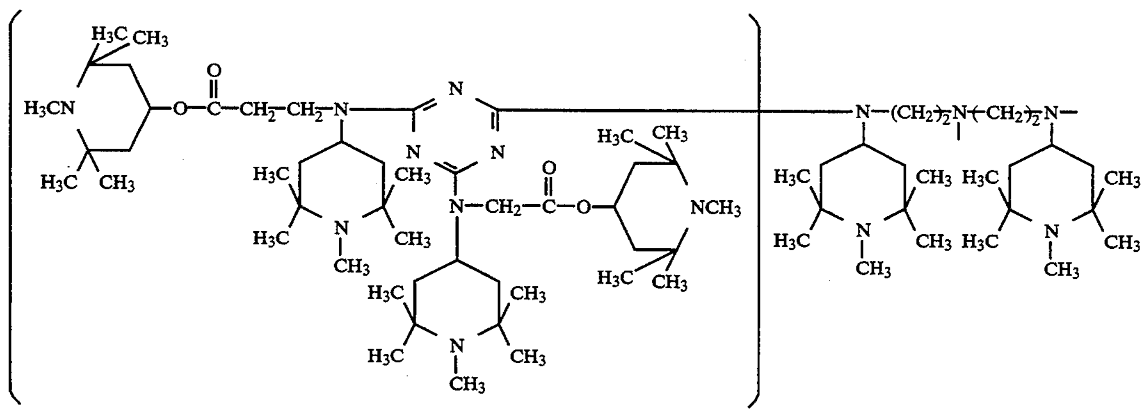

is prepared as described in Example 8, by reacting 40.9 g (0.015 mol) of the compound of Example 5 with 6.9 g (0.23 mol) of paraformaldehyde and 9.6 g (0.21 mol) of formic acid in 200 ml of t-amyl alcohol.

The product obtained melts at 194°–197° C.

Analysis for $C_{165}H_{300}N_{32}O_{12}$ Calculated: C=67.77%, H=10.34%, N=15.33% Found: C=67.30%, H=10.27%, N=15.21%

EXAMPLE 11

The compound of the formula

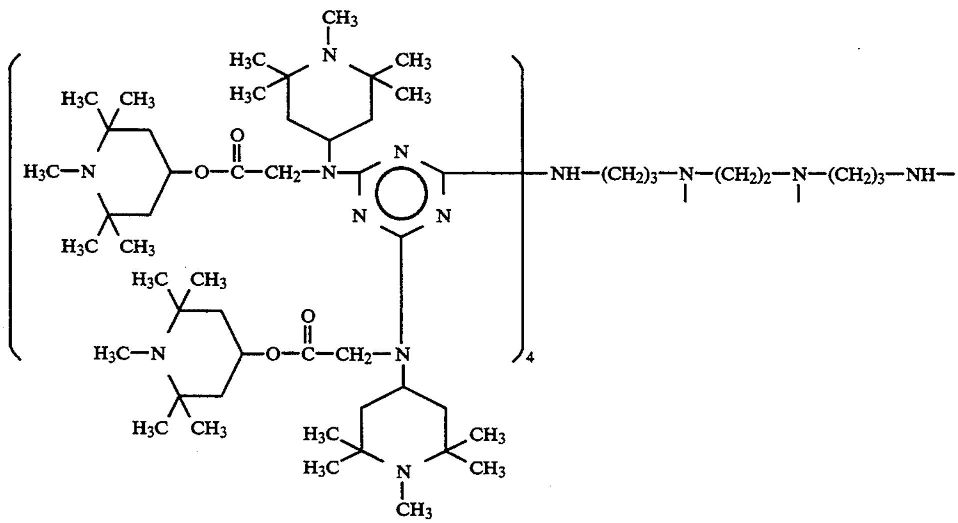

is prepared as described in Example 8, by reacting 24.8 g (0.0075 mol) of the compound from Example 6 with 4.5 g (0.15 mol) of paraformaldehyde and 6.9 g (0.15 mol) of formic acid in 200 ml of t-amyl alcohol.

The product obtained melts at 168°–170° C.

Analysis for $C_{196}H_{354}N_{40}O_{16}$ Calculated: C=66.74%, H=10.12%, N=15.88% Found: C=66.39%, H=10.08%, N=15.68%

EXAMPLE 12

(Light-stabilizing action in polypropylene fibres) 2.5 g of each of the products indicated in Table 1, 1 g of tris(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°–230° C. to give polymer granules which are then converted into fibres, using a pilot-type apparatus (Leonard-Sumirago (VA) Italy) operating under the following conditions:

Extruder temperature: 200°–230° C.
Head temperature: 255°–260° C.
Stretch ratio: 1:3.5
Count: 11 dtex per filament.

The fibres thus prepared are exposed, mounted on a white card, in a model 65 WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

Fibres prepared under the same conditions as indicated above, but without addition of the stabilizers according to the invention, are exposed for comparison.

The results obtained are shown in Table 1.

TABLE 1

| Stabilizer | $T_{50}$ (hours) |
|---|---|
| none | 240 |
| Compound from Example 1 | 2410 |

TABLE 1-continued

| Stabilizer | $T_{50}$ (hours) |
| --- | --- |
| Compound from Example 3 | 2030 |
| Compound from Example 4 | 2180 |
| Compound from Example 7 | 2300 |
| Compound from Example 8 | 2400 |
| Compound from Example 9 | 2180 |

EXAMPLE 13

Antioxidant action in polypropylene plaques.

1 g of the compound indicated in Table 2, 0.5 g of octadecyl 3-(3,5-di-t-butyl-4-hydroxyphenyl)-propionate, 1 g of tris(2,4-di-t-butylphenyl)phosphite and 1 g of calcium stearate are mixed in a slow mixer with 1000 g of polypropylene powder of melt index=2.1 g/10 minutes (measured at 230° C. and 2.16 kg).

The mixtures are extruded at 200°-220° C. to give polymer granules which are then converted into plaques of 1 mm thickness by injection-moulding at 220° C.

The plaques are then punched by means of a DIN 53451 mould, and the specimens obtained are exposed in a forced-circulation air oven maintained at a temperature of 135° C.

The specimens are tested at intervals by folding them by 180°, in order to determine the time (in hours) needed to cause fracture.

Specimens prepared under the same conditions as indicated above, but without addition of compounds of the present invention, are exposed for comparison. The results obtained are shown in Table 2.

TABLE 2

| Stabilizer | Time to fracture (in hours) |
| --- | --- |
| without stabiliser | 510 |
| Compound from Example 1 | 1470 |
| Compound from Example 8 | 1380 |

What is claimed is:

1. A compound of the formula (I)

(I)

in which $R_1$ is hydrogen, $C_1$-$C_8$alkyl, O, OH, $CH_2CN$, $C_1$-$C_{18}$alkoxy, $C_5$-$C_{12}$cycloalkoxy, $C_3$-$C_6$alkenyl, $C_7$-$C_9$phenylalkyl unsubstituted or mono-, di- or tri-substituted on the phenyl by $C_1$-$C_4$alkyl, or aliphatic $C_1$-$C_8$acyl, A is —O— or $R_6$—N— with $R_6$ being hydrogen or $C_1$-$C_{12}$alkyl, $R_2$ is $C_1$-$C_{10}$alkylene, $R_3$ is hydrogen, $C_1$-$C_{18}$alkyl, $C_5$-$C_{12}$cycloalkyl unsubstituted or mono-, di- or tri-substituted by $C_1$-$C_4$alkyl, $C_7$-$C_9$phenylalkyl unsubstituted or mono-, di- or tri-substituted on the phenyl by $C_1$-$C_4$alkyl, tetrahydrofurfuryl or a group of the formula (II)

(II)

where $R_7$ is as defined for $R_1$ or $C_2$-$C_4$alkyl substituted in the 2-,3- or 4-position by $C_1$-$C_8$alkoxy, by di($C_1$-$C_4$alkyl)amino or by a group of the formula (III)

(III)

where $Q_1$ is a direct bond, —O—, —$CH_2$—, —$CH_2CH_2$— or $CH_3$—N—, or $R_3$ is also a group of the formula (IV)

(IV)

$R_4$ is a group of the formula (V)

(V)

or a group of the formula (III) or one of the groups of the formulae (VIa)-(VIe)

$R_8$—N(—$R_9$)— (VIa)

$R_{10}$—O— (VIb)

(VIc)

-continued

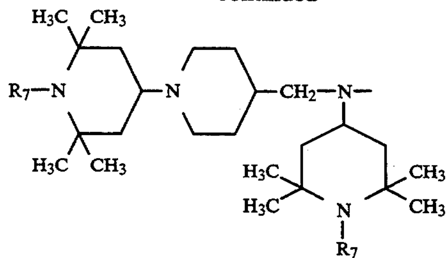

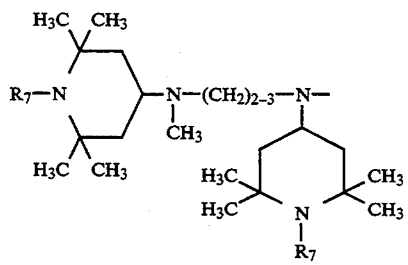

in which $R_7$ is as defined above, $R_8$, $R_9$ and $R_{10}$ which can be identical or different are as defined for $R_3$, or $R_{10}$ is also $C_3$–$C_{18}$alkenyl or phenyl unsubstituted or mono-, di- or tri-substituted by $C_1$–$C_4$alkyl or $C_1$–$C_4$alkoxy, $Q_2$ is —CO—, —$CH_2CH_2$—, —COCO—, —$CH_2CO$— or —$COCH_2CO$— and p is zero or 1, n is 2, 3 or 4 and, if n is 2, $R_5$ is one of the groups of the formulae (VIIa)-(VIIc)

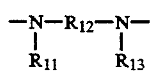

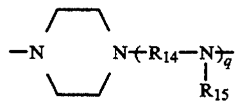

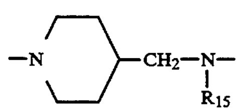

in which $R_{11}$, $R_{13}$ and $R_{15}$ which can be identical or different are as defined for $R_3$, or $R_{11}$ and $R_{13}$ are also a group of the formula (IV), $R_{12}$ is $C_2$–$C_{12}$alkylene, $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene), phenylenedi($C_1$–$C_4$alkylene) or $C_4$–$C_2$alkylene interrupted by a 1,4-piperazinediyl group or by 1, 2 or 3 oxygen atoms or by 1 or 2

$R_{16}N-$
| groups, where $R_{16}$ is as defined for $R_3$ or is aliphatic $C_1$–$C_{12}$acyl or ($C_1$–$C_{12}$alkoxy)carbonyl, or $R_{12}$ is also a group $R_{14}$ and $R_{17}$ are $C_2$–$C_6$alkylene and q is zero or 1, and if n is 3, $R_5$ is a group of the formula (VIIIa) or (VIIIb)

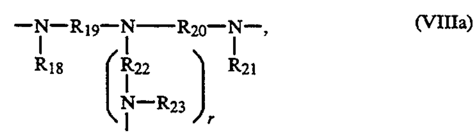

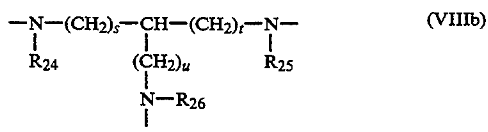

in which $R_{18}$, $R_{21}$, $R_{23}$, $R_{24}$, $R_{25}$ and $R_{26}$ which can be identical or different are as defined above for $R_{11}$ and $R_{13}$, $R_{19}$, $R_{20}$ and $R_{22}$ which can be identical or different are $C_2$–$C_6$alkylene, r and u are zero or 1, and s and t which can be identical or different are integers from 2 to 6, and, if n is 4, $R_5$ is a group of the formula (IX)

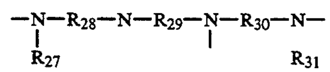

in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_6$alkylene.

2. A compound of the formula (I) according to claim 1, in which $R_1$ and $R_7$ are hydrogen, $C_1$–$C_4$alkyl, OH, $C_6$–$C_{12}$alkoxy, $C_5$–$C_8$cycloalkoxy, allyl, benzyl or acetyl.

3. A compound of the formula (I) according to claim 1, in which A is —O— or $R_6-N-$
| with $R_6$ being hydrogen or $C_1$–$C_{10}$alkyl, $R_2$ is $C_1$–$C_{10}$alkylene, $R_3$ is hydrogen, $C_1$–$C_{14}$alkyl, $C_5$–$C_8$cycloalkyl unsubstituted or mono-, di- or tri-substituted by $C_1$–$C_4$alkyl, benzyl unsubstituted or mono-, di- or tri-substituted on the phenyl by $C_1$–$C_4$alkyl, tetrahydrofurfuryl, a group of the formula (II), $C_2$–$C_3$alkyl substituted in the 2- or 3-position by $C_1$–$C_4$alkoxy, by di($C_1$–$C_4$alkyl)amino or by a group of the formula (III), where $Q_1$ is a direct bond, —O—, —$CH_2$— or —$CH_2CH_2$—, or $R_3$ is also a group of the formula (IV), $R_4$ is a group of the formula (V) or a group of the formula (III) or one of the groups of the formulae (VIa)-(VIe), in which $R_8$, $R_9$ and $R_{10}$ which can be identical or different are as defined for $R_3$, or $R_{10}$ is also $C_3$–$C_{12}$alkenyl or phenyl unsubstituted or mono-, di- or tri-substituted by $C_1$–$C_4$alkyl or $C_1$–$C_4$alkoxy, $Q_2$ is —CO—, —$CH_2CH_2$—, —COCO— or —$COCH_2CO$—, p is zero or 1 and n is 2, 3 or 4, and, if n is 2, $R_5$ is one of the groups of the formulae (VIIa)-(VIIc) in which $R_{11}$, $R_{13}$ and $R_{15}$ which can be identical or different are as defined above for $R_3$ or $R_{11}$ and $R_{13}$ are also a group of the formula (IV), $R_{12}$ is $C_2$–$C_{10}$alkylene, cyclohexylene, cyclohexylenedimethylene, methylenedicyclohexylene, phenylenedimethylene, $C_4$–$C_{10}$alkylene interrupted by a 1,4-piperazinediyl group or by 1, 2 or 3 oxygen atoms or by 1 or 2

$$R_{16}-\underset{|}{N}-$$

groups where $R_{16}$ is as defined above for $R_3$ or is aliphatic $C_1$–$C_8$acyl or ($C_1$–$C_8$alkoxy)carbonyl, or $R_{12}$ is also a group

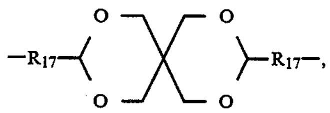

$R_{14}$ and $R_{17}$ are $C_2$–$C_4$alkylene and q is zero or 1, and, if n is 3, $R_5$ is a group of the formula (VIIIa) or (VIIIb), in which $R_{18}$, $R_{21}$, $R_{23}$, $R_{24}$, $R_{25}$ and $R_{26}$ which can be identical or different are as defined above for $R_{11}$ and $R_{13}$, $R_{19}$, $R_{20}$ and $R_{22}$ which can be identical or different are $C_2$–$C_4$alkylene, r and u are zero or 1 and s and t which can be identical or different are integers from 3 to 6 and, if n is 4, $R_5$ is a group of the formula (IX) in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_4$alkylene.

4. A compound of the formula (I) according to claim 1, in which A is —O— or $$R_6-\underset{|}{N}-$$

with $R_6$ being hydrogen or $C_1$–$C_8$alkyl, $R_2$ is $C_1$–$C_8$alkylene, $R_3$ is hydrogen, $C_1$–$C_2$alkyl, cyclohexyl unsubstituted or mono-, di- or tri-substituted by $C_1$–$C_4$alkyl, benzyl, tetrahydrofurfuryl, a group of the formula (II), $C_2$–$C_3$alkyl substituted in the2- or 3-position by methoxy, by ethoxy, by dimethylamino, by diethylamino or by a 4-morpholinyl group, or $R_3$ is also a group of the formula (IV), $R_4$ is a group of the formula (V) or a 4-morpholinyl group or one of the groups of the formulae (VIa)-(VIe) in which $R_8$, $R_9$ and $R_{10}$ which can be identical or different are as defined above for $R_3$, or $R_{10}$ is also $C_3$–$C_{11}$alkenyl or phenyl, $Q_2$ is —CO—, —$CH_2CH_2$— or —COCO—, p is zero or 1 and n is 2, 3 or 4, and, if n is 2, $R_5$ is one of the groups of the formulae (VIIa)-(VIIc) in which $R_{11}$, $R_{13}$ and $R_{15}$ which can be identical or different are as defined above for $R_3$, or $R_{11}$ and $R_{13}$ are also a group of the formula (IV), $R_2$ is $C_2$–$C_8$alkylene, cyclohexylenedimethylene, methylenedicyclohexylene, phenylenedimethylene, $C_4$–$C_{10}$alkylene interrupted by a 1,4-piperazinediyl group or by 1, 2 or 3 oxygen atoms or 2 by 1 or

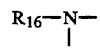

groups, where $R_{16}$ is as defined above for $R_3$ or is aliphatic $C_1$–$C_4$acyl or ($C_1$–$C_4$alkoxy)carbonyl, or $R_{12}$ is also a group

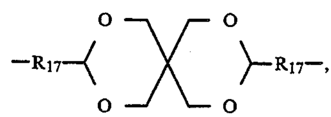

$R_{14}$ and $R_{17}$ are $C_2$–$C_4$alkylene and q is zero or 1, and, if n is 3, $R_5$ is a group of the formula (VIIIa) or (VIIIb) in which $R_{18}$, $R_{21}$, $R_{23}$, $R_{24}$, $R_{25}$ and $R_{26}$ which can be identical or different are as defined above for $R_{11}$ and $R_{13}$, $R_{19}$, $R_{20}$ and $R_{22}$ which can be identical or different are $C_2$–$C_4$alkylene, r and u are zero or 1 and s and t which can be identical or different are integers from 3 to 5, and, if n is 4, $R_5$ is a group of the formula (IX) in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_4$alkylene.

5. A compound of the formula (I) according to claim 1, in which A is —O— or $$R_6-\underset{|}{N}-$$

with $R_6$ being hydrogen or $C_1$–$C_4$alkyl, $R_2$ is $C_1$–$C_5$alkylene, $R_3$ is hydrogen, $C_1C_8$alkyl, cyclohexyl, a group of the formula (II) or a group of the formula (IV), $R_4$ is a group of the formula (V) or a 4-morpholinyl group or one of the groups of the formulae (VIa)-(VIe) in which $R_8$, $R_9$ and $R_{10}$ which can be identical or different are as defined above for $R_3$, $Q_2$ is —CO— or —$CH_2CH_2$—, p is zero or 1 and n is 2, 3 or 4, and, if n is 2, $R_5$ is one of the groups of the formulae (VIIa)-(VIIc) in which $R_{11}$, $R_{13}$ and $R_5$ which can be identical or different are as defined above for $R_3$, or $R_{11}$ and $R_{13}$ are also a group of the formula (IV), $R_{12}$ is $C_2$–$C_6$alkylene, cyclohexylenedimethylene, methylenedicyclohexylene, $C_6$–$C_{10}$alkylene interrupted by a 1,4-piperazinediyl group or by 2 or 3 oxygen atoms or by a group

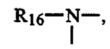

where $R_{16}$ is as defined above for $R_3$, $R_{14}$ is $C_2$–$C_3$alkylene and q is zero or 1, and, if n is 3, $R_5$ is a group of the formula (VIIa) or (VIIIb) in which r is zero, $R_{18}$, $R_{21}$, $R_{24}$, $R_{25}$ and $R_{26}$, which can be identical or different are as defined above for $R_{11}$ and $R_{13}$, $R_{19}$ and $R_{20}$ which can be identical or different are $C_2$–$C_3$alkylene, u is zero or 1 and s and t which can be identical or different are integers from 3 to 5, and, if n is 4, $R_5$ is a group of the formula (IX) in which $R_{27}$ and $R_{31}$ which can be identical or different are as defined above for $R_{11}$ and $R_{13}$, and $R_{28}$, $R_{29}$ and $R_{30}$ which can be identical or different are $C_2$–$C_3$alkylene.

6. A compound of the formula (I) according to claim 1, in which $R_1$ and $R_7$ are hydrogen or methyl, A is —O— or —NH—, $R_2$ is $C_1$–$C_2$alkylene, $R_3$ is hydrogen, $C_1C_4$alkyl, 2,2,6,6-tetramethyl-4-piperidyl or 1,2,2,6,6-pentamethyl-4-piperidyl, $R_4$ is a group of the formula (V) or a group of the formula (VIa) or (VIb) in which $R_8$ and $R_9$ which can be identical or different are as defined above for $R_3$, $R_{10}$ is 2,2,6,6-tetramethyl-4-piperidyl or 1,2,2,6,6-pentamethyl-4-piperidyl and n is 2, 3 or 4, and, if n is 2, $R_5$ is a group

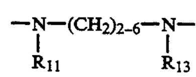

or a group

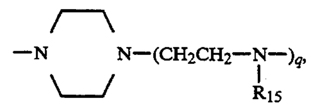

in which $R_{11}$, $R_{13}$ and $R_{15}$ which can be identical or different are as defined above for $R_3$, and q is zero or 1, and, if n is 3, $R_5$ is a group

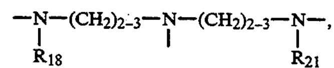

and, if n is 4, $R_5$ is a group

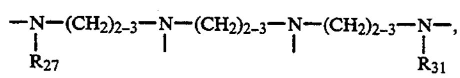

and $R_{18}$, $R_{21}$, $R_{27}$ and $R_{31}$ are as defined above for $R_3$.

* * * * *